(12) United States Patent
Takahashi (10) Patent No.: US 7,913,344 B2
(45) Date of Patent: Mar. 29, 2011

(54) ELECTRIC INTER-DENTAL BRUSH

(76) Inventor: Atsushi Takahashi, Tsuruga (JP)

( * ) Notice: Subject to any disclaimer, the term of this patent is extended or adjusted under 35 U.S.C. 154(b) by 1269 days.

(21) Appl. No.: 10/533,044

(22) PCT Filed: Jul. 23, 2003

(86) PCT No.: PCT/IB03/03452
§ 371 (c)(1),
(2), (4) Date: Nov. 14, 2005

(87) PCT Pub. No.: WO2004/037113
PCT Pub. Date: May 6, 2004

(65) Prior Publication Data
US 2006/0143842 A1    Jul. 6, 2006

(30) Foreign Application Priority Data

Oct. 28, 2002  (JP) ................................ 2002-312191
Dec. 27, 2002  (JP) ................................ 2002-382623

(51) Int. Cl.
*A61C 17/26* (2006.01)
*A61C 15/00* (2006.01)
(52) U.S. Cl. ............................................ 15/23; 15/22.1

(58) Field of Classification Search ............. 15/23, 22.1, 15/28, 24, 29
See application file for complete search history.

(56) References Cited

U.S. PATENT DOCUMENTS

| | | | | |
|---|---|---|---|---|
| 3,241,168 | A * | 3/1966 | McMaster et al. | 15/22.1 |
| 3,945,076 | A * | 3/1976 | Sung | 15/22.1 |
| 5,561,881 | A * | 10/1996 | Klinger et al. | 15/22.1 |
| 5,699,575 | A * | 12/1997 | Peifer | 15/23 |
| 5,934,908 | A * | 8/1999 | Woog et al. | 433/216 |
| 6,845,537 | B2 * | 1/2005 | Wong | 15/22.1 |
| 2002/0116775 | A1 * | 8/2002 | Wong | 15/22.1 |
| 2006/0143842 | A1 * | 7/2006 | Takahashi | 15/23 |

* cited by examiner

Primary Examiner — Lee D Wilson (57) ABSTRACT

Disclosed is an electric inter-dental brush device which is generally divided into a cleaning brush attached at a head assembly of the electric inter-dental brush device, a finger grip of a small size for holding a small-sized motor for driving the cleaning brush and a housing for holding a battery or AC adaptor for the small-sized motor and other components and parts of the electric inter-dental brush device. The finger grip and the housing are physically separated except through an electric cord connecting the small-sized motor and the battery or AC adaptor.

6 Claims, 12 Drawing Sheets

ELECTRIC INTER-DENTAL BRUSH

DESCRIPTION OF THE PRIOR ART

This invention relates to an electric toothbrush, and more particularly an electric inter-dental brush of a finger grip type having a freely detachable brush at its tip end.

In general, an electrical toothbrush having a motor providing power or drive and battery or an AC adapter was self contained, and compared to a conventional toothbrush, it was heavier and bulkier.

Due to the larger shape or bulkiness and heavier weight of the electrical toothbrush when compared to a conventional toothbrush, the usage sensation felt by the user was different from the conventional hand help/propelled toothbrush. This made it more difficult to utilize the existing finger-based brushing techniques. When the user relied more on the power generated by the movement of the brush, it was possible to lower the amount of plaque removable on a section by section basis. Especially with inter-dental space brush, the awkwardness associated with the weight and bulkiness made it more difficult to properly perform the brushing without a soft/tender touch so the user did not damage the gum. Also it is desirable to have the equipment waterproofed for daily usage.

SUMMARY OF THE INVENTION

Accordingly, it is an object of the present invention to provide an electric toothbrush of a finger grip type suitable for inter-dental brushing techniques.

It is another object of the present invention to provide an electric toothbrush of a finger grip type having a detachable and light-weight cleaning brush at its tip end for allowing the user to utilize the existing finger-relied inter-dental brushing techniques.

It is still another object of the present invention to provide an electric inter-dental brush device of a finger grip type including a finger grip for containing a source of drive therein and a detachable cleaning brush powered by the source of drive.

It is still another object of the present invention to provide an electric inter-dental brush device of a finger grip and rewinding type including a finger grip for holding a source of drive and a detachable cleaning brush powered by the source of drive and a rewindable electrical connection cord or wire connected between the source of drive and the cleaning brush.

In a preferred embodiment of the present invention, en electric inter-dental brush device utilizes a small-sized motor or ultrasonic vibrator as a source of drive to be housed in a finger grip of a small-sized cylindrical shape for powering a cleaning brush to be secured at a tip end of the electric inter-dental brush device. An output section of the electric inter-dental brush device is designed to provide an appropriate amount or form of output drive to the cleaning brush by increasing or decreasing the output of rotating power, or by converting the output power into rotating movement, repeating movement, sliding movement, or a combination of two or more of these movements.

If the ultrasonic vibrator is used instead of the small-sized motor, an output section of the ultrasonic vibrator is housed inside the finger grip. The driving power generated from the output section is transferred through a cleaning brush shaft which at one end away from the output section is the cleaning brush. The shaft penetrates through a head assembly of the electric inter-dental brush device. The head assembly is connected to the finger grip of the electric inter-dental brush device through a coupling section which allows the head assembly to be removable from the finger grip. When the user uses the electric inter-dental brush device for oral cavity cleaning, the finger grip thereof can easily be held by fingers and provide maneuverability and usage sensation equivalent to a conventional (non-electric) toothbrush or an inter-dental space brush.

Electricity to run the small-sized motor or ultrasonic vibrator is provided from a battery or batteries or from an AC converter adapter which is housed in a casing or housing of the electric inter-dental brush device. Electrical cords or wires to provide electricity to the motor or to the ultrasonic vibrator are to be adjusted at an appropriate length. A waterproofed spool assembly is housed within the housing to rewind the electrical cords or wires, contain components or parts for an electrical power supply. This arrangement is effective in increasing the portability of the electric inter-dental brush device. A space in the housing for the wound cord is enclosed. A cover is designed to cover up and enclose the space for the wound cord, the housing of the electric inter-dental brush device. The head assembly and the cover may be put on or removed directly to and from the housing.

BRIEF DESCRIPTION OF THE DRAWINGS

Other objects and features of the present invention will become apparent from the following detailed-description considered in connection with the accompanying drawings which discloses the embodiments of the present invention. It should be understood, however, that the drawings are designed for the purposes of illustration only and not as a definition of the limits of the invention.

In the drawings, wherein similar reference characters denote similar elements throughout the several views:

FIGS. 9(A) to 9(C) are exploded views of a head assembly in the electric inter-dental brush device according to the present invention;

FIGS. 10(A) to 10(H) are front, side and cross-sectional views of individual components of the head assembly;

FIGS. 12(A) to 12(F) are schematic diagrams showing operation of safety switches; and FIGS. 13(A) to 13(G) are views showing operation of another example of safety switches.

DETAILED DESCRIPTION OF PREFERRED EMBODIMENTS

Turning now in detail to the drawings, the figures shows an electric inter-dental brush device according to several embodiments of the present invention.

Figure 1:
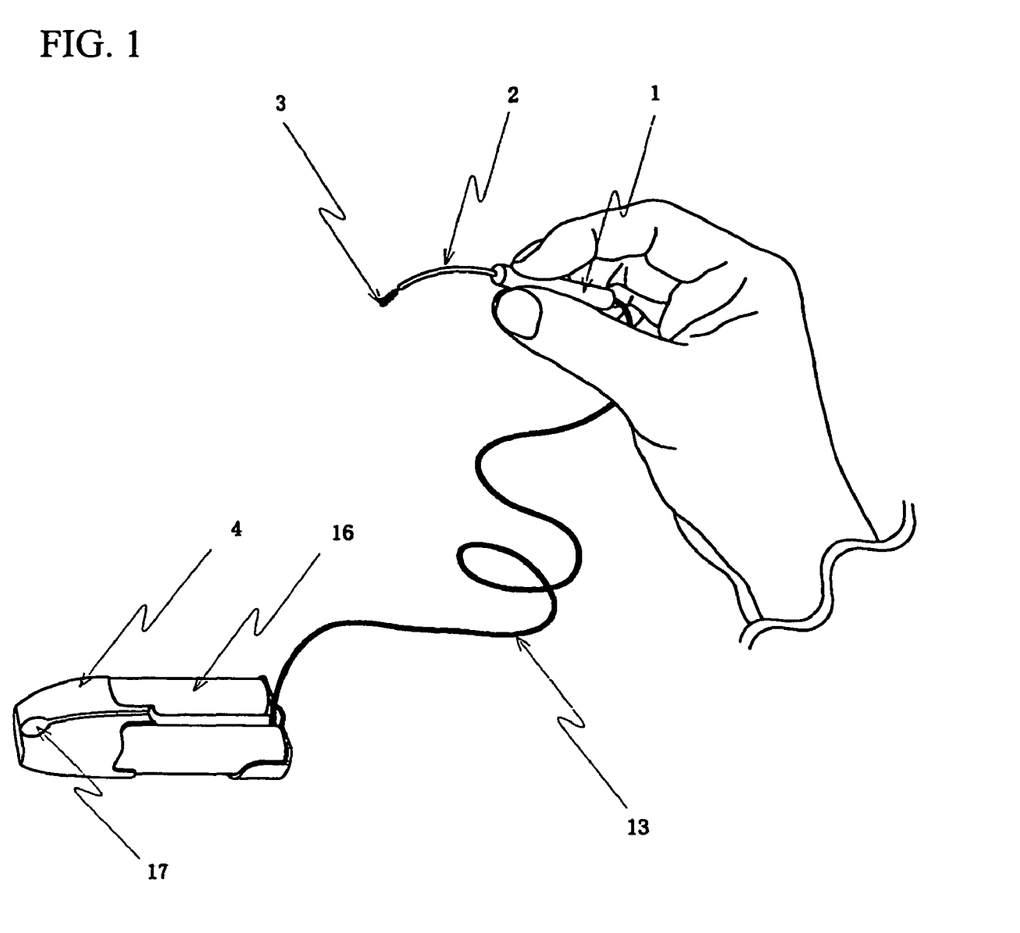
FIG. 1 is a perspective view showing the condition where an electric inter-dental brush device according to the present invention is in use.
Figure 6:
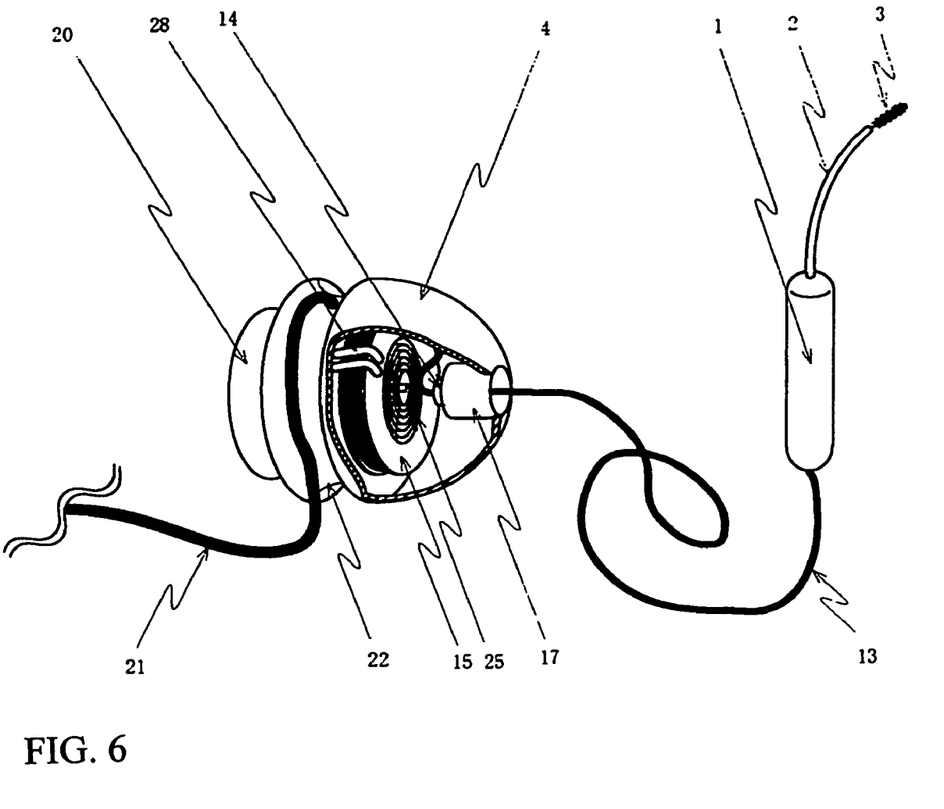
FIG. 6 is a partially cut-away view of the electric inter-dental brush device as shown in FIG. 5.
Figure 8:
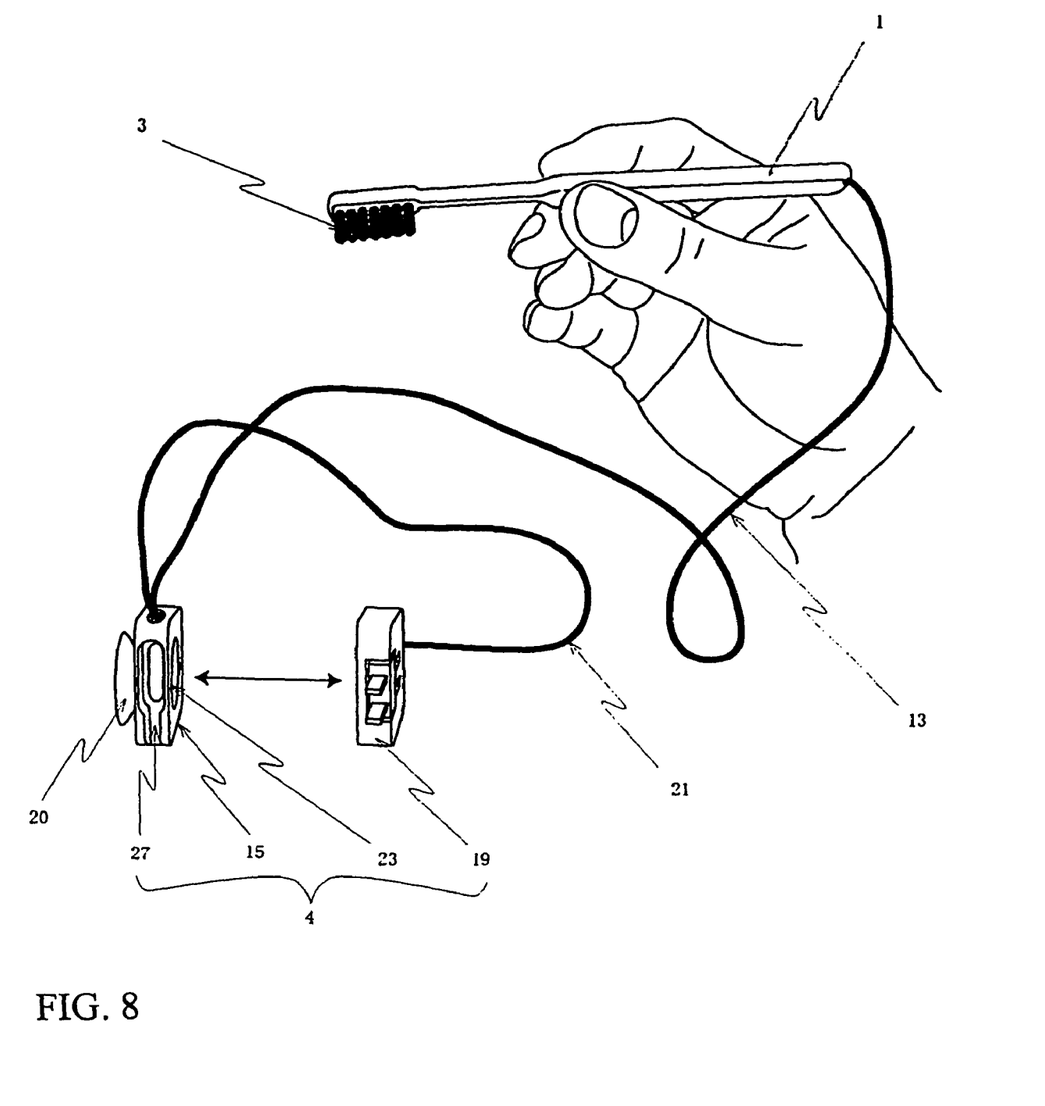
FIG. 8 is a perspective view of the electric inter-dental brush device according to still another embodiment of the present invention.

FIGS. 1, 6, and 8 illustrates the electric inter-dental brush device according to three embodiments of the present invention. The electric inter-dental brush device as illustrated therein is generally divided into a cleaning brush 3 attached at a head assembly of the electric inter-dental brush device, a finger grip 1 of a small size for holding a source of drive for driving the cleaning brush 3 and a housing 4 for holding a power supply for the drive source and other components and parts of the electric inter-dental brush device. As illustrated in FIG. 1, a small-sized motor 5 (FIG. 2) or an ultrasonic vibrator 24 (as in FIG. 8) is provided as source of electric drive for powering the cleaning brush 3.

An output section (gear box) 6 of the motor 5 is self contained in the finger grip 1 to transfer the output from such driving device to the detachable brush head assembly 2, which contains the cleaning brush 3 located at the tip of the head assembly 2. The head assembly 2 containing the cleaning brush 3 is detachable from the finger grip 1 for replacements of the cleaning brush 3. An electric supply 16 (a battery or batteries in FIG. 3) supplying electric power to the small-sized motor is physically separated from the finger grip 1 except via an electric cord 13 connecting the small-sized motor 5 and the electric supply 16. The electric supply 16 is contained within the housing 4. The housing 4 contains an electrical cord rewinding device, wherein the electrical cord 13 is stored. All components or parts of the electric supply 16 are also contained in the housing 4 to improve portability and shape. The housing 4 has a space or recess for receiving the finger grip 1 and another space or recess for the head assembly 2.

Figure 9:
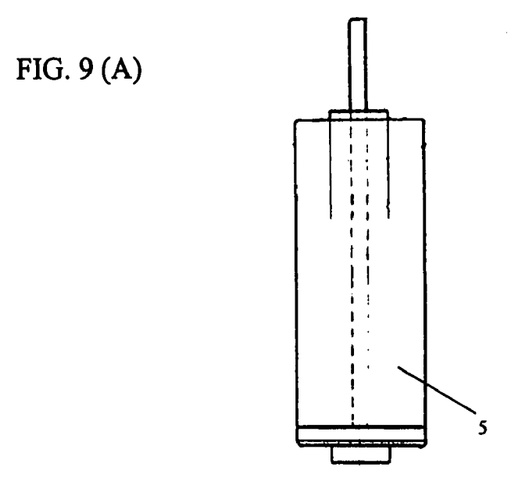
Figure 10:
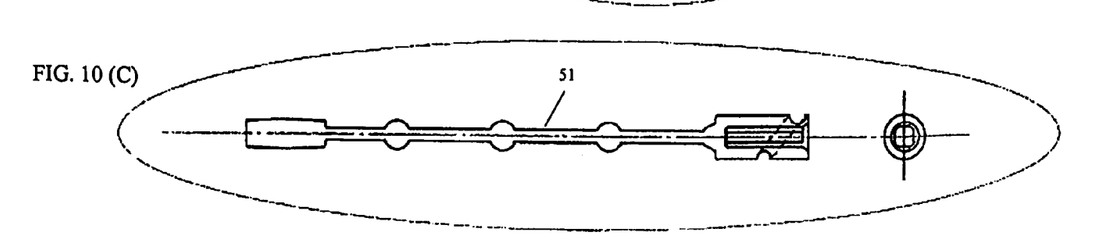
Figure 11:
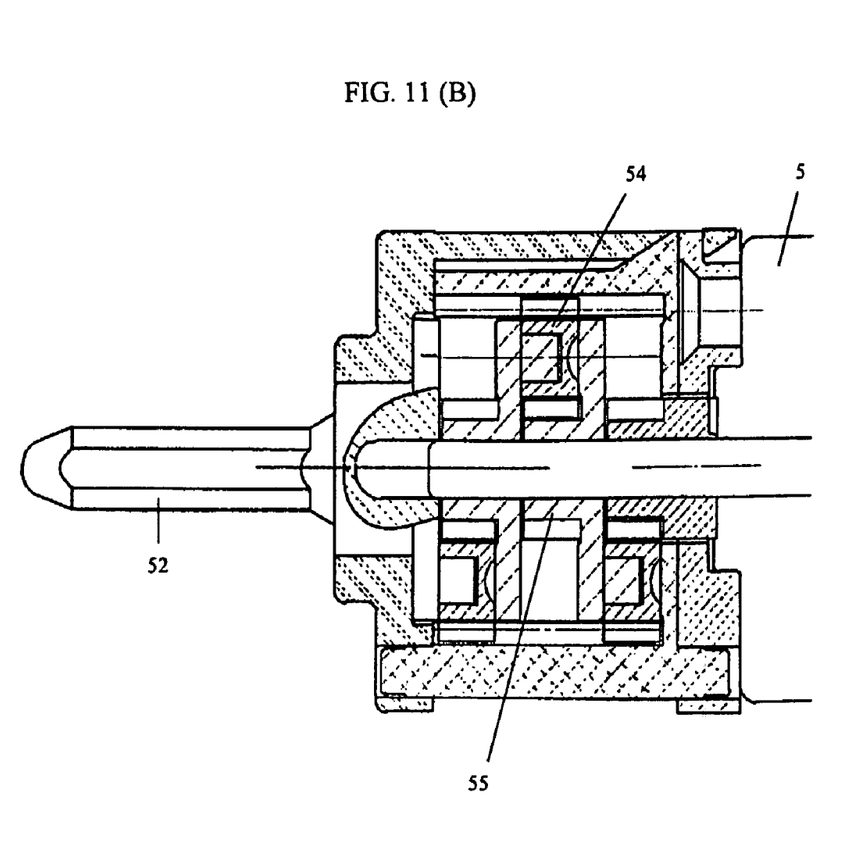
FIGS. 11(A) and 11(B) are enlarged assembled and cross-sectional views of the head assembly.
Figure 12:
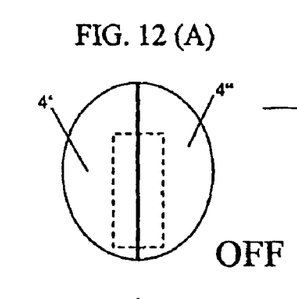

While FIG. 9(A) shows the small-sized motor 5 of a diameter of 5.4 mm, for example, FIG. 9(B) shows in more detail the finger grip 1 and the head assembly 2 and FIG. 9(C) shows a cross sectional view of the head assembly 2. As more clearly illustrated in FIGS. 10(A) to 10(H), the head assembly 2 includes an up-down movement shaft 51 to which the cleaning brush 3 is attached. The up-down movement shaft 51 is also coupled with the small-sized motor 5 for rotational movement so that the shaft 51 carries out not only up-down movement but also rotational movement. The output section (gear box) located between the up-down movement shaft 51 and the small-sized motor 5 includes a carrier output shaft 52, a carrier 53, a desired number of planet gears 54, a sun gear 55 at the center of the planet gears 54, and an inner gear 56. The gear box comprising those gears is secured between an output shaft set cover 57 and a motor bracket 58. The output box 6 when assembled is illustrated in more detail in FIGS. 11(A) and 11(B).

If the number of the planet gears 54 is changed, then the number of revolutions and revolution torque of the gear box are made adjustable. When the number of planet gears 54 is three, for example, reduction of revolution speed will be ⅟20. Should the gear box be of a cartridge type, an electric inter-dental brush may be made adjustable for different rates of revolutions, even with the same voltage and same motor. As long as the user purchases an electric inter-dental brush, he or she may use or adjust that one for his or her best brushing position and brushing technique.

The driving mechanism for up-down movement and rotation is also shown and described in PCT application PCT/JP02/04510 "UNIVERSAL ANGLE ELECTRIC ORAL CLEANING DEVICE", filed on May 9, 2002 by the same applicant, the disclosure of which is incorporated by reference.

As shown in FIG. 1, the electric supply 16 is physically separated, making the whole of the electric inter-dental brush device light in weight and compact, and provides maneuverability and usage sensation similar to the popular hand held inter-dental brush. The established finger-based brushing technique for manual (non-electric) brushes may be used with the present invention, particularly because the finger grip 1 for housing the drive device is light in weight and may be held by fingers.

Figure 2:
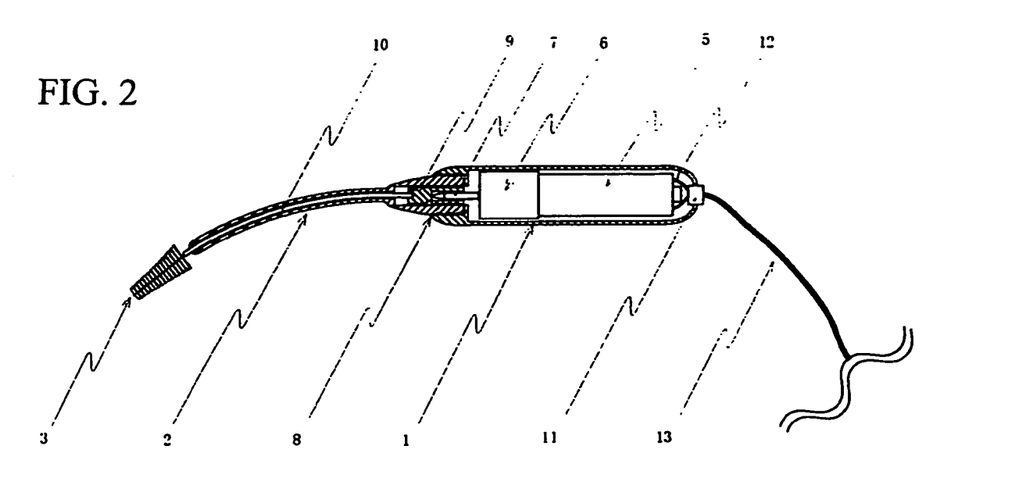
FIG. 2 is a cross sectional side view of the electric inter-dental brush device as shown in FIG. 1.

As shown in FIG. 2, the head assembly 2 having the cleaning brush 3 at its tip end is flexible and has a rotational phase relative to the finger grip 1. The rotational phase of the head assembly 2 may be set at several different pre-set angles or a removable joint 8 between the finger grip 1 and the head assembly 2 itself may be adjustable at an appropriate angle desired by the user. Therefore, in addition the head assembly 2 having the cleaning brush 3 is also detachable, allowing the angle between the cleaning brush and the finger grip 1 may be adjusted according to the desired area of cleaning.

Within the finger grip 1, there are located the small-sized motor 5, and the power output device (gear box) 6. In the embodiment of FIG. 8, the ultrasonic vibrator 24 is located within the finger grip 1. Drive force from the shaft 7 is transferred to the joint 8, and a cam mechanism 9 to convert the rotating movement into one or combination of rotating movement, repeating movement, sliding movement or repeating movement. The resulting movement is finally transferred to the cleaning brush through a slider 10 which penetrates through the head assembly 2 of the electric inter-dental brush device.

A water resistant packing 11 is attached to the other end of the finger grip 1, and an electric cord or wire 13 is pulled into the finger grip 1 and attached to an input terminal 12 of the motor through this water resistant packing 11.

Figure 3:
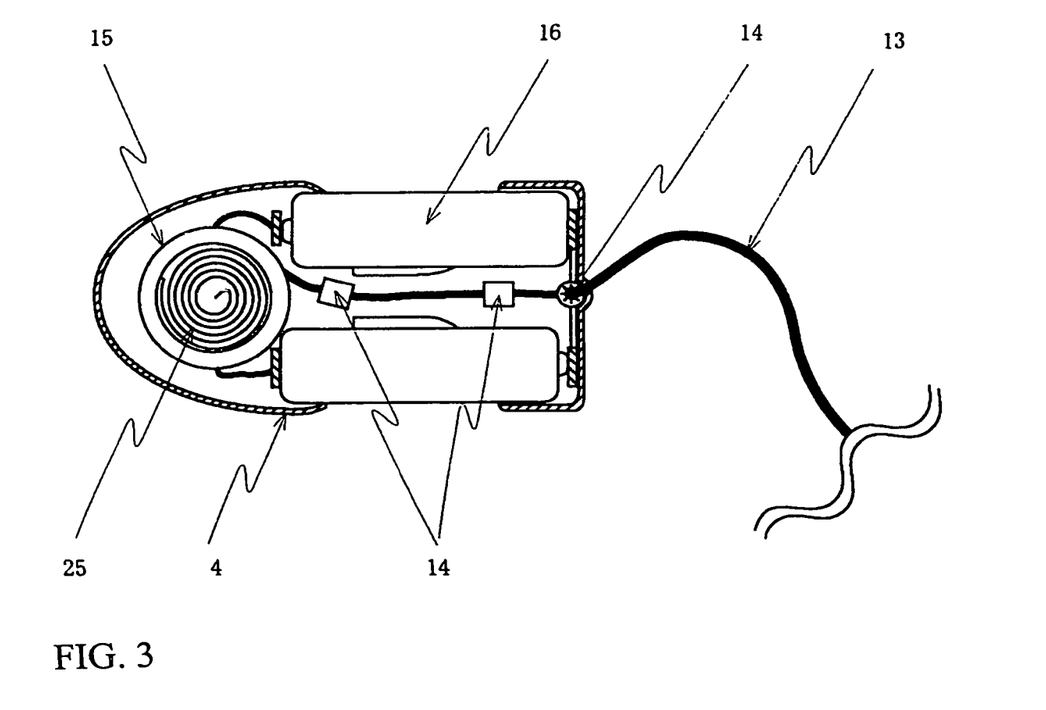
FIG. 3 is a cross sectional plain view of a housing of the electric inter-dental brush device as shown in FIG. 1.
Figure 4:
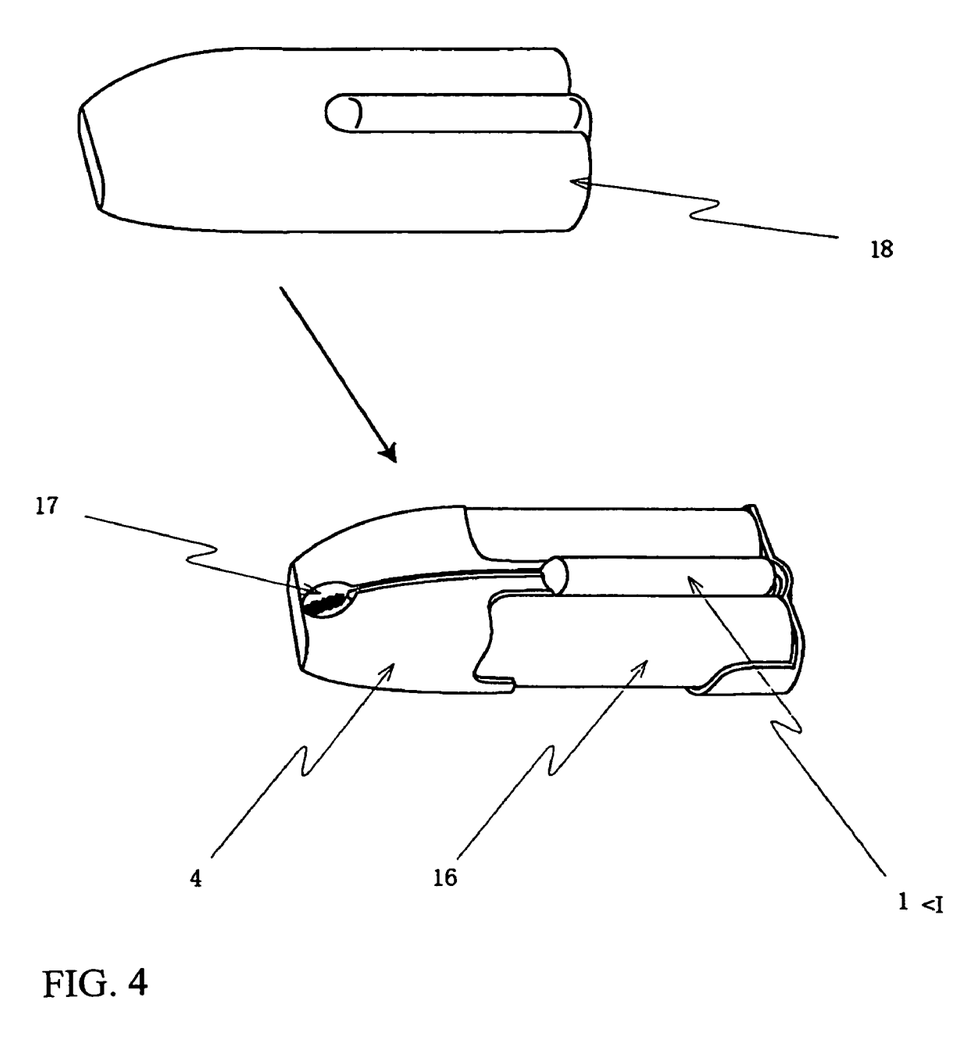
FIG. 4 is an exploded perspective view of the housing as shown in FIG. 3.

This electric cord 13, as illustrated in FIG. 3, is stored in an electric cord rewinding assembly 15, with a water repelling packing 14 in the housing as a guide for the electric cord. The electric cord rewinding assembly 15 adjusts the length of the electric cord 13 to an appropriate length and a terminal secured at the back side of the electric cord rewinding assembly 15 is used for attachment to the battery or batteries (electrical power supply or power source) 16.

Figure 5:
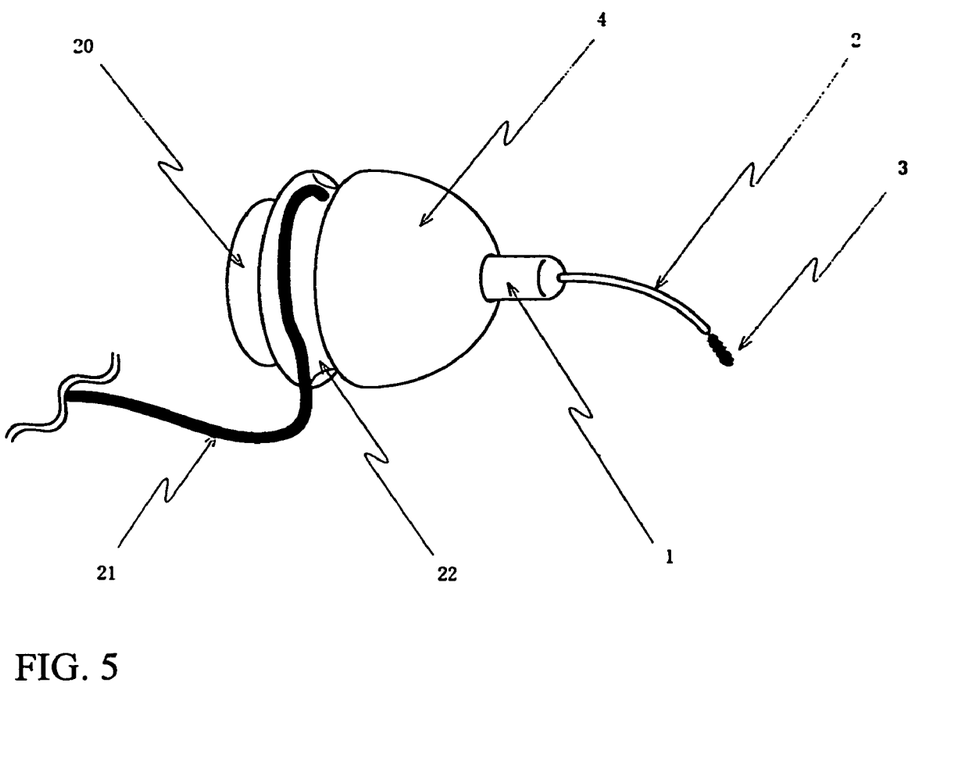
FIG. 5 is a perspective view of the electric inter-dental brush device with a suction cup according to another embodiment of the present invention.

When the electric inter-dental brush device is used as a portable device, as shown in FIG. 5, the finger grip 1 and the head assembly 2 having the cleaning brush 3 are held in spaces or recesses in the housing 17, while the electric cord 13 is wound in the electric cord rewinding assembly 15. A housing cover 18 is attached as protection to prevent the finger grip 1, the head assembly 2 and the cleaning brush 3 from contamination.

FIGS. 12(A) to 12(F) show another example of the housing 4 with a safety switch mechanism wherein the housing 4 is shaped like a breakable egg with a left half 4' and a right half 4" with a couple of switches 30 and 31. The switches 30 and 31 are connected in series between the motor 5 and the power supply or batteries 16 for safety purposes. The first switch 31 is turned OFF only when pushed by the head assembly 2, whereas the second switch 32 is OFF when the housing 4 is open and ON when the housing 13 is closed. That is, power is supplied to the motor 5 only when the housing 4 is closed and the head assembly 2 is pulled out from the housing 4.

When the housing 4 is held by the user and one click opened by the left hand, for example, the housing 4 is opened so that the head assembly 2 may be pulled out of the housing 4 by the right hand. Once the housing 4 is then one click closed, the head assembly 2 starts operating. When the housing 4 is gripped again after use, the housing 4 is opened to turn OFF the second switch 32. Therefore, safety is secured against misuse because the head assembly 2 operates only when the housing 4 is closed and the head assembly 2 is pulled out of the housing 4.

Figure 13:
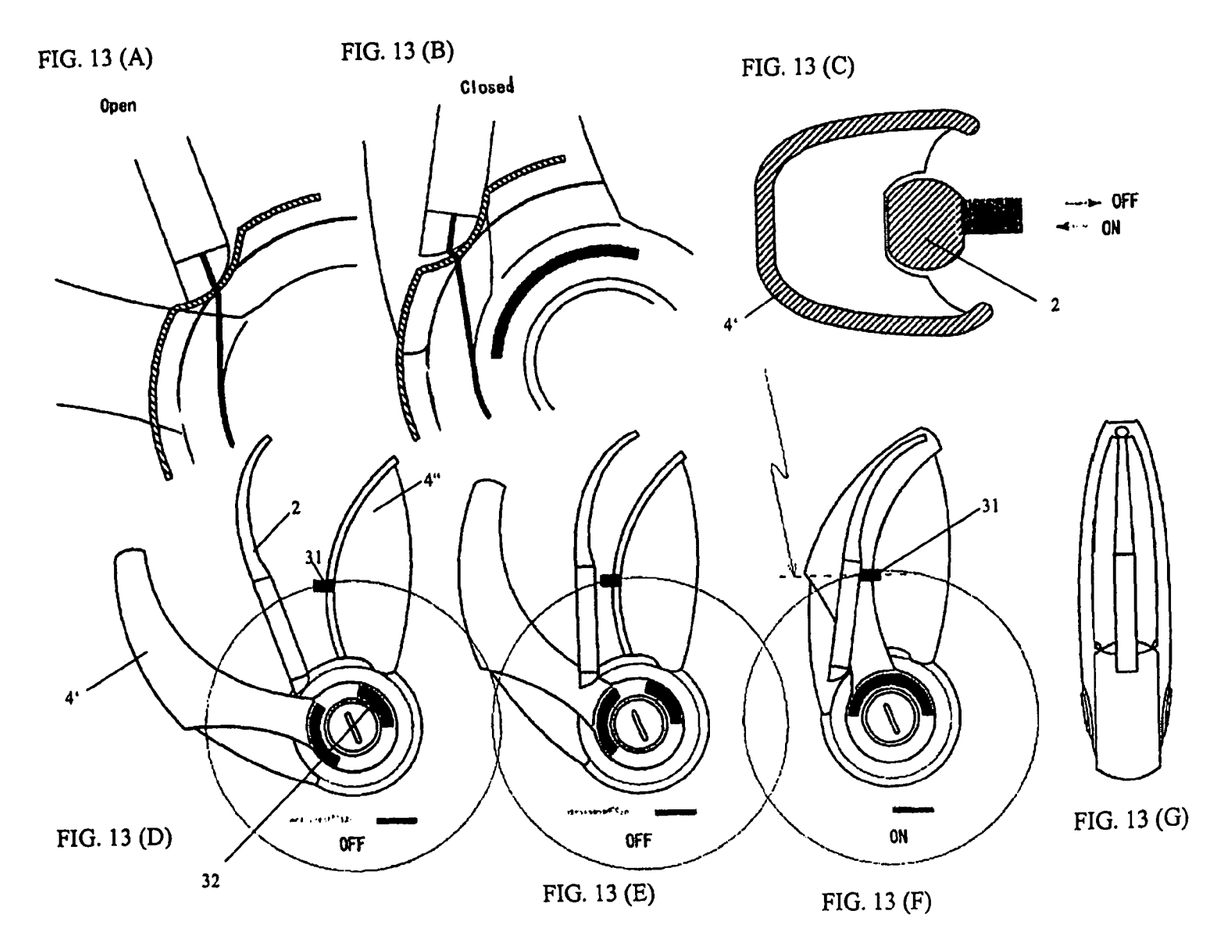

It is noted that as shown in FIGS. 13(D) to 13(F) the head assembly 2 is positioned with stability because the bottom of the housing 4 is curved in a certain direction. Even when the electric cord 13 is rewound into the rewinding assembly 15, the head assembly 2 will keep stable and will not turn in a certain direction.

The shape of the housing 4 shown in FIGS. 5 and 6 may be designed to be permanently attached to improve portability. When this shape and design is used, an AC adapter 19 and the electric cord rewinding assembly 15, which can adjust the length of the unwound electrical cord to an appropriate length, are both housed inside the housing 4. A suction cup 20 is attached on the back side of the housing 4. For example, the housing 4 may be attached to a surface of bathroom sink or a mirror surface. An AC adapter cord 21 is connected to a household AC electric outlet as shown in FIG. 6. The electric cord 13 is wound up by the electrical cord rewinding assembly 15, while the finger grip 1 remains fitted closely to the housing 4.

Figure 7:
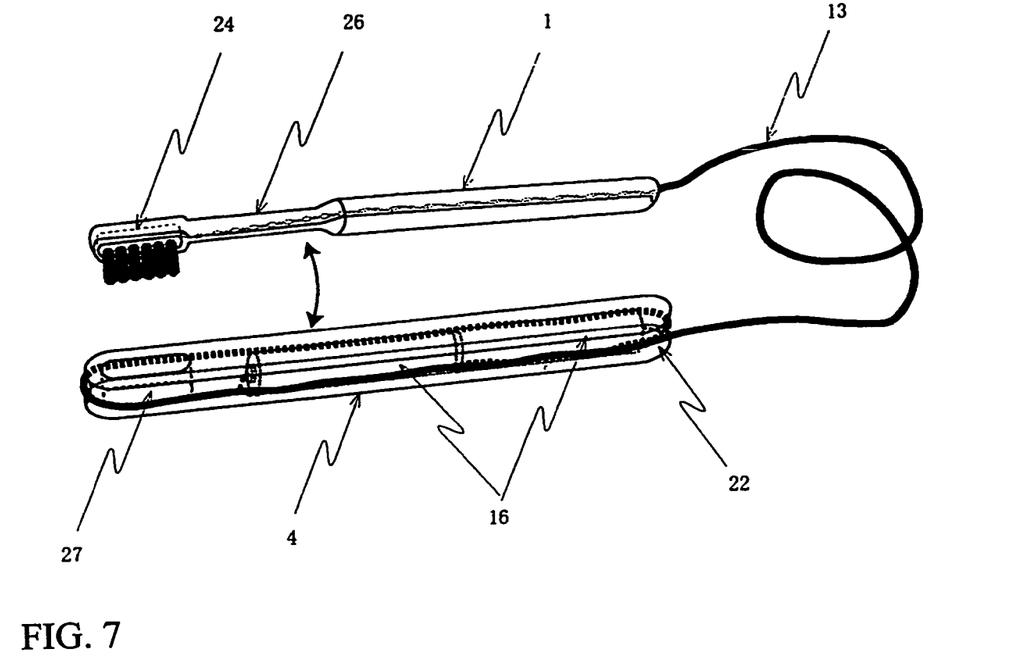
FIG. 7 is a perspective view of the electric inter-dental brush device according to another embodiment of the present invention.

The housing 4 is held by the suction cup 20 to the mirror or other surfaces, as shown in FIG. 6. Under this condition, the finger grip 1 may be pulled out with the cord extending to an appropriate length and a rotation switch mechanism 28 secured on the electrical cord rewinding assembly 15 is automatically activated, so that the user can immediately start the process to clean the oral cavity. The cleaning brush 3 is kept dry when not in use, to prevent growth of caries and other bacteria, the causes of gum diseases which are bacteria that do not like dry or airy environment. An electric cord rewinding wheel 22 is located at the bottom of the housing 4 for winding and holding an AC adapter cord 21. This arrangement makes the electric inter-dental brush device compact and makes the same not bulky and easy to change location of where the electric inter-dental brush device is set up.

Where the ultrasonic vibrator 24 is used as the source of driving the cleaning brush 3, its electric power supply may still be separated as shown in FIG. 7. Therefore the outer shape of the electric inter-dental brush device as shown in FIG. 7 may be similar to the outer shape of a conventional hand-held inter-dental (non-electric) brush. The shape of the housing 4 is shaped to fit the finger grip 1 and a head arm 26. The electric cord 13 is wound and stored in the electrical cord winding wheel 22 and the cleaning brush 3 is held in a storage space in the housing 4.

As the ultrasonic vibrator 24 may be applicable to inter-dental brush, as shown in FIG. 8, the housing 4 may be divided into a first division for the AC adapter 19 with an electric cord and a second division for the electric cord rewinding mechanism 15. The housing 4 may be made highly portable by making the first and second divisions of the housing 4 detachable. When the device is in use, the first and second divisions of the housing 4 are separated and the AC adapter cord 21 and the power supply electric cord 13 are pulled out from the electric cord rewinding mechanism 15. The AC adapter 19 is plugged into an electric utility outlet and the electrical cord rewinding mechanism 15 is affixed to a mirror or other surface by a suction cup or other means. Because the AC adapter which is relatively heavy is secured on the mirror or other surface, the negative effect towards the brushing technique is avoided. When the electrical cord rewinding mechanism 15 is maintained at the same height as the height of the oral cavity, the weight of the electric cord 13 is also reduced by half, allowing the user to practice intricate brushing technique.

When a brush holding mechanism is formed or installed on the housing 4, the cleaning brush 3 may be kept dry as shown in FIG. 5 to prevent the growth of caries and bacteria that cause periodontal disease, which do not prefer dry and ventilated area for growth. As shown in FIG. 8, the AC adapter cord 21 and the electric cord 13 are stored in the electric cord rewinding device 15. The AC adapter 19 and the electric cord rewinding device 15 is combined into as one unit with the aid of a joint mechanism 23. In the embodiment of FIG. 7 wherein the battery or batteries (electrical power supply) 16 is kept within the housing 4, the electrical cord 13 is wound onto the perimeter of the winding wheel 22. The portability of the electric inter-dental brush device is increased by installing a brush holding mechanism (not shown) on the housing 4.

The shape of the cleaning brush 3 of the electric inter-dental brush device with the rewinding cord according to the embodiments of the present invention is not to be limited to the illustrations and suggestions described above. It should be noted that the finger grip 1, the battery or batteries (electric power supply) 16, the AC adapter 19 and the electrical cord rewinding assembly 15 may be combined in other ways as well as certain changes and improvements may be made, so long as it is within the spirit and scope of the present invention.

According to the illustrated embodiments of the present invention, the portion of the electric inter-dental portable electrical brush with the rewinding cord, to be held by the hand of the user is small and light weight. More particularly, the finger grip may be similar in shape and size to a conventional hand-held inter-dental brush to allow the user the maneuverability and usage sensation that is equal to the conventional hand-held inter-dental brush and allow the user to practice the established brushing technique. In addition, the housing 4 may be equipped with a water repelling packing or gasket for daily use.

While only a few embodiments of the present invention have been shown and described, it is to be understood that many changes and modifications may be made thereunto without departing from the spirit and scope of the invention as defined in the appended claims.

What is claimed is:

1. An electric dental brush device comprising:
   a finger grip;
   a drive source disposed in the finger grip;
   a housing separated from the finger grip;
   a power supply disposed in the housing and always connected to the drive source; and
   a cleaning brush secured at a tip portion of the electric dental brush device, the cleaning brush being driven by the drive source.

2. The electric dental brush device of claim 1, wherein the drive source comprises a small-sized motor for driving the cleaning brush.

3. The electric dental brush device of claim 1, wherein the cleaning brush is freely removable from the finger grip.

4. An electric dental brush device comprising:
   a finger grip;
   a drive source disposed in the finger grip;
   a housing separated from the finger grip;
   a power supply disposed in the housing and always connected to the drive source;
   a cleaning brush secured at a tip portion of the electric dental brush device; and a connection member always connecting the drive source and the power supply for powering the cleaning brush.

5. An electric dental brush device comprising:

a finger grip;

a drive source disposed in the finger grip;

a housing separated from the finger grip and freely opened or closed;

a power supply disposed in the housing and always connected to the drive source;

a cleaning brush secured at a tip portion of the electric dental brush device, the cleaning brush being powered by the drive source; and a switch mechanism for allowing power supply to the cleaning brush only when the housing is closed and the cleaning brush is out of the housing.

6. The electric dental brush device of claim 5, wherein a plurality of planer gears for reducing the revolution speed of the drive source is connected to the drive source.

\* \* \* \* \*